(12) United States Patent
Pryor et al.

(10) Patent No.: US 12,370,320 B2
(45) Date of Patent: Jul. 29, 2025

(54) ACCESSORY DEVICES, SYSTEMS, AND METHODS FOR MEDICINE ADMINISTRATION AND TRACKING

(71) Applicant: Medtronic MiniMed, Inc., Northridge, CA (US)

(72) Inventors: Jack D. Pryor, Ladera Ranch, CA (US); Andrew J. Childs, San Diego, CA (US); Ellis Garai, Woodland Hills, CA (US)

(73) Assignee: Medtronic MiniMed, Inc., Northridge, CA (US)

( * ) Notice: Subject to any disclaimer, the term of this patent is extended or adjusted under 35 U.S.C. 154(b) by 689 days.

(21) Appl. No.: 17/353,449

(22) Filed: Jun. 21, 2021

(65) Prior Publication Data
US 2022/0401656 A1    Dec. 22, 2022

(51) Int. Cl.
*A61M 5/315*    (2006.01)
*A61M 5/31*    (2006.01)
*A61M 5/32*    (2006.01)

(52) U.S. Cl.
CPC .... *A61M 5/31568* (2013.01); *A61M 5/31525* (2013.01); *A61M 5/31545* (2013.01); *A61M 5/3202* (2013.01); *A61M 2005/3125* (2013.01); *A61M 2205/502* (2013.01); *A61M 2205/584* (2013.01); *A61M 2205/587* (2013.01)

(58) Field of Classification Search
CPC .......... A61M 5/31568; A61M 5/31525; A61M 5/31545; A61M 5/3202; A61M 2005/3125
See application file for complete search history.

(56) References Cited

U.S. PATENT DOCUMENTS

| | | | |
|---|---|---|---|
| 4,755,173 | A | 7/1988 | Konopka et al. |
| 5,391,250 | A | 2/1995 | Cheney, II et al. |
| 5,485,408 | A | 1/1996 | Blomquist |
| 5,522,803 | A | 6/1996 | Teissen-Simony |
| 5,665,065 | A | 9/1997 | Colman et al. |
| 5,800,420 | A | 9/1998 | Gross et al. |
| 5,807,375 | A | 9/1998 | Gross et al. |
| 5,925,021 | A | 7/1999 | Castellano et al. |
| 5,954,643 | A | 9/1999 | Van Antwerp et al. |
| 6,017,328 | A | 1/2000 | Fischell et al. |
| 6,186,982 | B1 | 2/2001 | Gross et al. |
| 6,246,992 | B1 | 6/2001 | Brown |
| 6,248,067 | B1 | 6/2001 | Causey, III et al. |

(Continued)

OTHER PUBLICATIONS

Extended European Search Report issued in corresponding application EP 22178950.6 dated Oct. 25, 2022 (9 pages).

*Primary Examiner* — Dung T Ulsh
(74) *Attorney, Agent, or Firm* — Carter, DeLuca & Farrell LLP

(57) ABSTRACT

An accessory for use with a medicine delivery device includes a body configured to attach to a medicine delivery device and a user interface disposed on the body and configured to communicate information to a user. In aspects, the user interface includes first and second lights configured to be selectively illuminated and a first symbol associated with the first light. The first light and the first symbol together indicate an action to be performed when the first light is illuminated. In aspects, the user interface includes red, yellow, and green lights configured to be illuminated in sequential time periods after a dose using the medicine delivery device.

19 Claims, 10 Drawing Sheets

(56) References Cited

U.S. PATENT DOCUMENTS

| | | |
|---|---|---|
| 6,248,093 B1 | 6/2001 | Moberg |
| 6,355,021 B1 | 3/2002 | Nielsen et al. |
| 6,379,301 B1 | 4/2002 | Worthington et al. |
| 6,544,212 B2 | 4/2003 | Galley et al. |
| 6,558,351 B1 | 5/2003 | Steil et al. |
| 6,591,876 B2 | 7/2003 | Safabash |
| 6,641,533 B2 | 11/2003 | Causey, III et al. |
| 6,736,797 B1 | 5/2004 | Larsen et al. |
| 6,749,587 B2 | 6/2004 | Flaherty |
| 6,766,183 B2 | 7/2004 | Walsh et al. |
| 6,801,420 B2 | 10/2004 | Talbot et al. |
| 6,804,544 B2 | 10/2004 | Van Antwerp et al. |
| 7,003,336 B2 | 2/2006 | Holker et al. |
| 7,029,444 B2 | 4/2006 | Shin et al. |
| 7,066,909 B1 | 6/2006 | Peter et al. |
| 7,137,964 B2 | 11/2006 | Flaherty |
| 7,303,549 B2 | 12/2007 | Flaherty et al. |
| 7,399,277 B2 | 7/2008 | Saidara et al. |
| 7,442,186 B2 | 10/2008 | Blomquist |
| 7,602,310 B2 | 10/2009 | Mann et al. |
| 7,647,237 B2 | 1/2010 | Malave et al. |
| 7,699,807 B2 | 4/2010 | Faust et al. |
| 7,727,148 B2 | 6/2010 | Talbot et al. |
| 7,785,313 B2 | 8/2010 | Mastrototaro |
| 7,806,886 B2 | 10/2010 | Kanderian, Jr. et al. |
| 7,819,843 B2 | 10/2010 | Mann et al. |
| 7,828,764 B2 | 11/2010 | Moberg et al. |
| 7,879,010 B2 | 2/2011 | Nunn et al. |
| 7,890,295 B2 | 2/2011 | Shin et al. |
| 7,892,206 B2 | 2/2011 | Moberg et al. |
| 7,892,748 B2 | 2/2011 | Norrild et al. |
| 7,901,394 B2 | 3/2011 | Ireland et al. |
| 7,942,844 B2 | 5/2011 | Moberg et al. |
| 7,946,985 B2 | 5/2011 | Mastrototaro et al. |
| 7,955,305 B2 | 6/2011 | Moberg et al. |
| 7,963,954 B2 | 6/2011 | Kavazov |
| 7,977,112 B2 | 7/2011 | Burke et al. |
| 7,979,259 B2 | 7/2011 | Brown |
| 7,985,330 B2 | 7/2011 | Wang et al. |
| 8,024,201 B2 | 9/2011 | Brown |
| 8,100,852 B2 | 1/2012 | Moberg et al. |
| 8,114,268 B2 | 2/2012 | Wang et al. |
| 8,114,269 B2 | 2/2012 | Cooper et al. |
| 8,137,314 B2 | 3/2012 | Mounce et al. |
| 8,181,849 B2 | 5/2012 | Bazargan et al. |
| 8,182,462 B2 | 5/2012 | Stoc et al. |
| 8,192,395 B2 | 6/2012 | Estes et al. |
| 8,195,265 B2 | 6/2012 | Goode, Jr. et al. |
| 8,202,250 B2 | 6/2012 | Stutz, Jr. |
| 8,207,859 B2 | 6/2012 | Enegren et al. |
| 8,226,615 B2 | 7/2012 | Bikovsky |
| 8,257,259 B2 | 9/2012 | Brauker et al. |
| 8,267,921 B2 | 9/2012 | Yodfat et al. |
| 8,275,437 B2 | 9/2012 | Brauker et al. |
| 8,277,415 B2 | 10/2012 | Mounce et al. |
| 8,292,849 B2 | 10/2012 | Bobroff et al. |
| 8,298,172 B2 | 10/2012 | Nielsen et al. |
| 8,303,572 B2 | 11/2012 | Adair et al. |
| 8,305,580 B2 | 11/2012 | Aasmul |
| 8,308,679 B2 | 11/2012 | Hanson et al. |
| 8,313,433 B2 | 11/2012 | Cohen et al. |
| 8,318,443 B2 | 11/2012 | Norrild et al. |
| 8,323,250 B2 | 12/2012 | Chong et al. |
| 8,343,092 B2 | 1/2013 | Rush et al. |
| 8,352,011 B2 | 1/2013 | Van Antwerp et al. |
| 8,353,829 B2 | 1/2013 | Say et al. |
| 9,672,328 B2 | 6/2017 | Saint et al. |
| 10,835,727 B2 | 11/2020 | Montalvo et al. |
| 2005/0038332 A1* | 2/2005 | Saidara .......... G16H 40/67 128/920 |
| 2007/0123819 A1 | 5/2007 | Mernoe et al. |
| 2010/0160861 A1 | 6/2010 | Causey, III et al. |
| 2017/0182256 A1 | 6/2017 | Andersen et al. |
| 2019/0001067 A1 | 1/2019 | Berey et al. |
| 2019/0175841 A1 | 6/2019 | Sjolund et al. |
| 2019/0392937 A1 | 12/2019 | Mensinger et al. |
| 2020/0327973 A1* | 10/2020 | Pryor .......... G16H 40/67 |

* cited by examiner

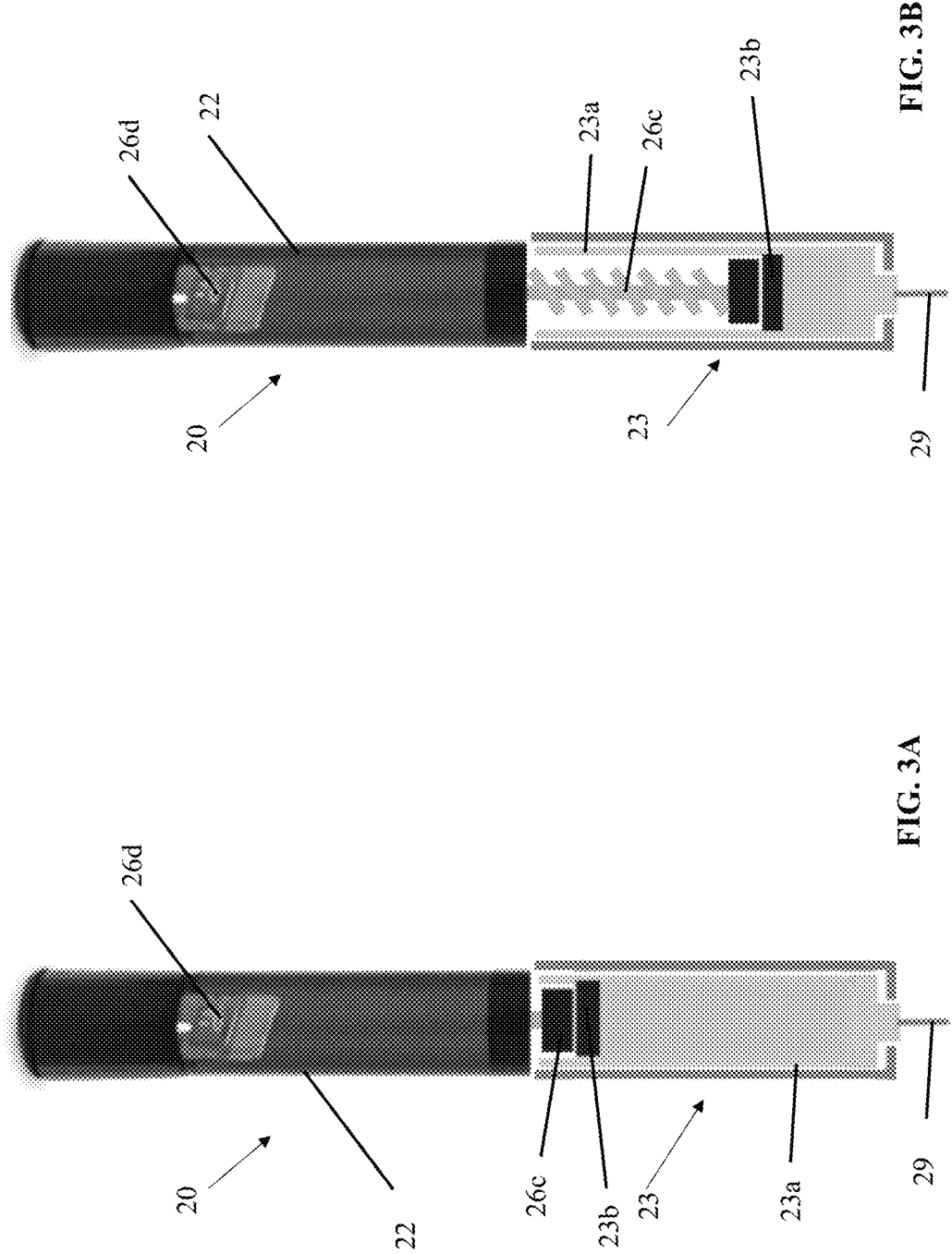

ACCESSORY DEVICES, SYSTEMS, AND METHODS FOR MEDICINE ADMINISTRATION AND TRACKING

FIELD

The present disclosure is related to medicine administration and tracking and, more specifically, to accessory devices, systems, and methods for medicine administration and tracking.

BACKGROUND

Diabetes mellitus ("diabetes") is a metabolic disease associated with high blood sugar due to insufficient production or use of insulin by the body. Diabetes affects hundreds of millions of people and is among the leading causes of death globally. Diabetes has been categorized into three types: type 1, type 2, and gestational diabetes. Type 1 diabetes is associated with the body's failure to produce sufficient levels of insulin for cells to uptake glucose. Type 2 diabetes is associated with insulin resistance, in which cells fail to use insulin properly. Gestational diabetes can occur during pregnancy when a pregnant woman develops a high blood glucose level. Gestational diabetes often resolves after pregnancy; however, in some cases, gestational diabetes develops into type 2 diabetes.

Various diseases and medical conditions, such as diabetes, require a user to self-administer doses of medicine. When administering a liquid medicine by injection, for example, the appropriate dose amount is set and then dispensed by the user, e.g., using a syringe, a medicine delivery pen, or a pump. Regardless of the particular device utilized for injecting the liquid medicine, it is important track medicine dosed and facilitate a user's compliance with a dosing regime, particularly for managing lifelong or chronic conditions like diabetes.

SUMMARY

Provided in accordance with aspects of the present disclosure is an accessory for use with a medicine delivery device. The accessory includes a body configured to attach to a medicine delivery device and a user interface disposed on the body and configured to communicate information to a user. The user interface includes first and second lights configured to be selectively illuminated and a first symbol associated with the first light. The first light and the first symbol together indicate an action to be performed when the first light is illuminated.

In an aspect of the present disclosure, the first light is a green light and the second light is a red light.

In another aspect of the present disclosure, the first light is a green light and the first symbol represents at least a portion of the medicine delivery device such that, when the green light is illuminated, the action to be performed of using the medicine delivery device is indicated.

In still another aspect of the present disclosure, the user interface further includes a second symbol associated with the second light. In such aspects, the second light and the second symbol together provide an indication to the user. More specifically, the second light may be a red light and the second symbol may be a stop symbol such that, when the red light is illuminated, the indication to the user is to stop and not proceed with using the medicine delivery device.

In yet another aspect of the present disclosure, the body is configured to releasably attached to the medicine delivery device. In such aspects, the body may be a cap configured to releasably cover a dispensing end of the medicine delivery device.

In still yet another aspect of the present disclosure, the accessory further includes at least one detector disposed within the body and configured to detect at least one of attachment of the cap with the medicine delivery device or detachment of the cap from the medicine delivery device.

In another aspect of the present disclosure, the user interface further includes a third light configured to be selectively illuminated. In such aspects, the first light may be a green light indicating it is safe to use the medicine delivery device to dose, the second light may be a red light indicating it is not safe to use the medicine delivery device to dose, and/or the third light may be a yellow light indicating the user to proceed with caution.

Another accessory for use with a medicine delivery device in accordance with the present disclosure includes a body configured to attach to a medicine delivery device, an electronics unit disposed within the body, and a user interface disposed on the body in communication with the electronics unit. The electronics unit is configured to at least one of receive or determine, with respect to a prior dose at time $t_0$, a first time $t_1$ after which it is safe to dose and a second time $t_2$ before which it is not safe to dose. The user interface includes a green light, a red light, and a yellow light. The electronics unit is configured to control the user interface to illuminate the red light between time $t_0$ and time $t_2$, extinguish the red light and illuminate the yellow light at time $t_2$, maintain the yellow light from time $t_2$ to time $t_1$, and extinguish the yellow light and illuminate the green light at time $t_1$.

In an aspect of the present disclosure, the electronics unit is further configured to control the user interface to maintain the green light from time $t_1$ until a subsequent dose is logged.

In another aspect of the present disclosure, times $t_0$, $t_1$, and $t_2$ are relative times (e.g., where $t_0=0$ or a start of a count-up timer) or clock times (e.g., actual times on a 12 hr or 24 hr clock).

In still another aspect of the present disclosure, the body is a cap configured to releasably cover a dispensing end of the medicine delivery device. In such aspects, at least one detector may be disposed within the body and configured to detect at least one of attachment of the cap with the medicine delivery device or detachment of the cap from the medicine delivery device.

In yet another aspect of the present disclosure, the electronics unit is configured to determine or receive a determination that a dose from the medicine delivery device has occurred based at least upon at least one of an attachment of the cap or a detachment of the cap.

In still yet another aspect of the present disclosure, the determination that a dose from the medicine delivery device has occurred is further based upon which light is illuminated. More specifically, no determination that a dose from the medicine delivery device has occurred may be made despite the at least one of attachment of the cap or detachment of the cap when the red light is illuminated. Alternatively or additionally, the determination that a dose from the medicine delivery device has occurred may be made based upon the at least one of attachment of the cap or detachment of the cap and other criteria when either the green light or the yellow light is illuminated. In aspects, the criteria when the green light is illuminated are different from the criteria when the yellow light is illuminated.

BRIEF DESCRIPTION OF DRAWINGS

FIGS. 3A and 3B are side, partial longitudinal, cross-sectional views of the medicine delivery device of FIG. 2 with the medicine cartridge in a full condition and the medicine cartridge in a partially emptied condition, respectively;

DETAILED DESCRIPTION

Figure 1B:
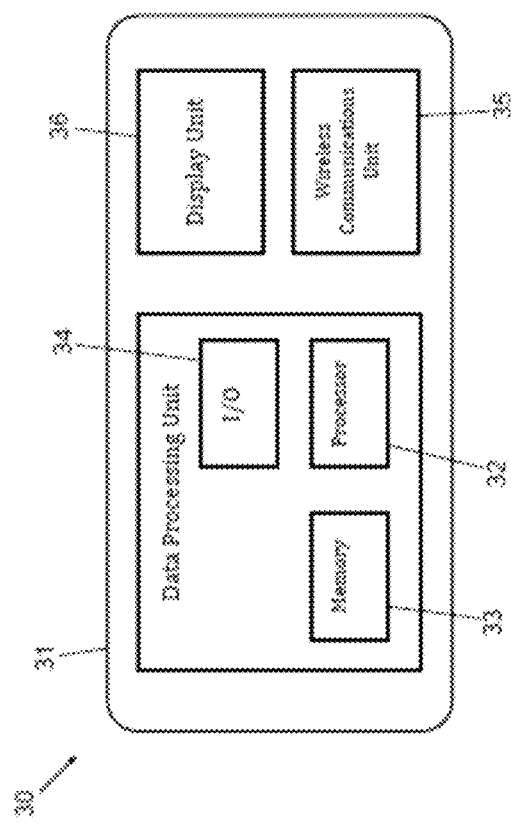
FIG. 1B is a block diagram of one configuration of the computing device of the system of FIG. 1A in accordance with the present disclosure.
Figure 1A:
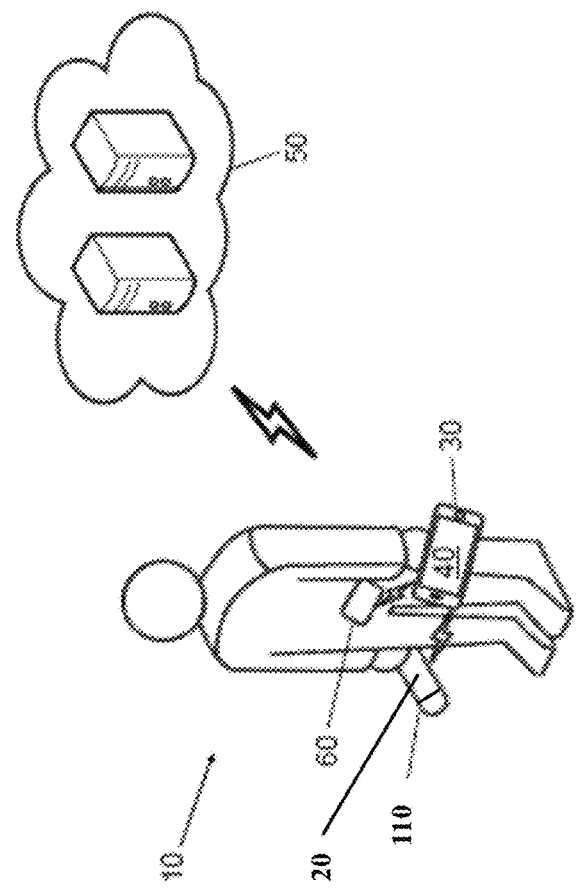
FIG. 1A is a schematic illustration of a medicine administration and tracking system provided in accordance with the present disclosure including a medicine delivery device, an accessory attached to the medicine delivery device, a computing device, and, in aspects, a sensor device and/or a data processing system.

FIG. 1A illustrates a medicine administration and tracking system 10 provided in accordance with the present disclosure including a medicine delivery device 20, a computing device 30 running a health management application 40, and an accessory device 110 configured to mechanically couple to medicine delivery device 20 and to wirelessly communicate with computing device 30 and/or other devices part of or connected to system 10. System 10, in aspects, further includes a data processing system 50 and/or a sensor device 60.

Medicine delivery device 20 is detailed and illustrated herein as a medicine delivery pen, although any other suitable medicine delivery device may be provided such as, for example, a syringe, a pump, etc. Pen 20, described in greater detail below, is operable to select, set, and/or dispense a dose of medicine, e.g., a dose of insulin. Pen 20 may be configured as a disposable device, e.g., wherein pen 20 is discarded once emptied of medicine, or a reusable device configured to enable refilling and/or replacement of a medicine cartridge thereof. Although referred to herein in the singular, it is understood that reference to pen 20 is not limited to single pen 20 but may apply to multiple pens 20 with which accessory device 110 is utilized.

Computing device 30 is detailed and illustrated herein as a smartphone, although any other suitable computing device may be provided such as, for example, a tablet, a wearable computing device (e.g., a smart watch, smart glasses, etc.), a laptop and/or desktop computer, a smart television, a network-based server computer, etc.

Accessory device 110 is detailed herein as a cap for selectively covering a dispensing end of pen 20, although other suitable accessory devices 110 configured, for example, to mechanically engage a body 22 of pen 20, facilitate holding pen 20 on a support surface (e.g., a table), facilitate retaining pen 20 during transport (e.g., in a user's pocket or bag), etc. are also contemplated.

Health management application 40 is paired with accessory device 110, which may be a prescription-only medical device for use with medicine delivery devices, e.g., pen 20, via smartphone 30, although other suitable configurations are also contemplated. In aspects, the pairing of smartphone 30 with accessory device 110 at least partially unlocks health management application 40 to enable the user to utilize some or all features of health management application 40, e.g., according to the user's prescription. Thus, the act of pairing can unlock and enable the functionality of health management application 40 and/or system 10 (including accessory device 110), while health management application 40 (and/or system 10) may provide only limited features in the absence of pairing with accessory device 110.

Health management application 40 of smartphone 30, in aspects, can monitor and/or control functionalities of accessory device 110 and provide a dose calculator module and/or decision support module that can calculate and recommend a dose of medicine for the user to administer using pen 20. Health management application 40 provides a user interface, on the user interface of smartphone 30, to allow a user to manage health-related data. For example, health management application 40 can be configured to control some functionalities of accessory device 110 and/or to provide an interactive user interface to allow a user to manage settings of accessory device 110 and/or settings for smartphone 30 that can affect the functionality of system 10. Smartphone 30 can additionally or alternatively be used to obtain, process, and/or display contextual data that can be used to relate to the health condition of the user, including the condition for which pen 20 is used to treat. For example, smartphone 30 may be operable to track the location of the user; physical activity of the user including step count, movement distance and/or intensity, estimated calories burned, and/or activity duration; and/or interaction pattern of the user with smartphone 30. In aspects, health management application 40 can aggregate and process the contextual data to generate decision support outputs, e.g., on the user interface and/or on accessory device 110, to guide and aid the user in monitoring their condition, using pen 20, and/or managing their behavior to promote treatment and better health outcomes.

In aspects, system 10 further includes a data processing system 50 in communication with accessory device 110 and/or smartphone 30. Data processing system 50 can include one or more computing devices in a computer system and/or communication network accessible via the internet, e.g., including servers and/or databases in the cloud. System 10 can additionally or alternatively include sensor device 60 to monitor one or more health metrics and/or physiological parameters of the user. Examples of health metric and physiological parameter data monitored by sensor device 60 include analytes (e.g., glucose), heart rate, blood pressure, user movement, temperature, etc. Sensor device 60 may be a wearable sensor device such as a continuous glucose monitor (CGM) to obtain transcutaneous or blood glucose measurements that are processed to produce continuous glucose values. For example, the CGM can include a glucose processing module implemented on a stand-alone display device and/or implemented on smartphone 30, which processes, stores, and displays the continuous glucose values for the user. Such continuous glucose values can be utilized by health management application 40, for example, for displaying health data, in dose calculation and/or decision support, etc.

FIG. 1B illustrates smartphone 30 of system 10 (FIG. 1A) including a data processing unit 31, a wireless communications unit 35, and a display unit 36. Data processing unit 31 includes a processor 32 to process data, a memory 33 in communication with the processor 32 to store data, and an input/output unit (I/O) 34 to interface processor 32 and/or memory 33 to other modules, units, and/or devices of smartphone 30 and/or external devices. Processor 32 can include a central processing unit (CPU) or a microcontroller unit (MCU). Memory 33 can include and store processor-executable code, which when executed by processor 32, configures the data processing unit 31 to perform various operations, e.g., such as receiving information, commands, and/or data, processing information and data, and transmitting or providing information/data to another device. In aspects, data processing unit 31 can transmit raw or processed data to data processing system 50 (FIG. 1A). To support various functions of data processing unit 31, memory 33 can store information and data, such as instructions, software, values, images, and other data processed or referenced by processor 32. For example, various types of Random Access Memory (RAM) devices, Read Only Memory (ROM) devices, Flash Memory devices, and other suitable storage media can be used to implement storage functions of memory 33. I/O 34 of data processing unit 31 can interface data processing unit 31 with wireless communications unit 35 to utilize various types of wired or wireless interfaces compatible with typical data communication standards, for example, which can be used in communications of data processing unit 31 with other devices such as pen 20, via a wireless transmitter/receiver (Tx/Rx), e.g., including, but not limited to, Bluetooth, Bluetooth low energy, Zigbee, IEEE 802.11, Wireless Local Area Network (WLAN), Wireless Personal Area Network (WPAN), Wireless Wide Area Network (WWAN), WiMAX, IEEE 802.16 (Worldwide Interoperability for Microwave Access (WiMAX)), 3G/4G/LTE cellular communication methods, NFC (Near Field Communication), and parallel interfaces. I/O 34 of data processing unit 31 can also interface with other external interfaces, sources of data storage, and/or visual or audio display devices, etc. to retrieve and transfer data and information that can be processed by processor 32, stored in memory 33, and/or exhibited on an output unit of smartphone 30 and/or an external device. For example, display unit 36 of smartphone 30 can be configured to be in data communication with data processing unit 31, e.g., via I/O 34, to provide a visual display, an audio display, and/or other sensory display that produces the user interface of the health management application 40 (FIG. 1A). In some examples, display unit 36 can include various types of screen displays, speakers, or printing interfaces, e.g., including but not limited to, light emitting diode (LED), or liquid crystal display (LCD) monitor or screen, cathode ray tube (CRT) as a visual display; audio signal transducer apparatuses as an audio display; and/or toner, liquid inkjet, solid ink, dye sublimation, inkless (e.g., such as thermal or UV) printing apparatuses, etc.

Smartphone 30 can receive dose and related information (e.g., which can include time information, dose setting information, and/or dose dispensing information) via manual entry by the user and/or automatically from a connected tracking device (within or associated with pen 20, accessory device 110, and/or other connected device(s)). Upon receipt of the dose and related information, smartphone 30 stores the information in memory 33, e.g., which can be included among a list of doses or dosing events. In aspects, via the user interface associated with health management application 40, smartphone 30 allows the user to browse a list of previous doses, to view an estimate of current medicine active in the user's body (medicine on board, e.g., insulin on board) based on calculations performed by health management application 40, and/or to utilize a dose calculation module to assist the user regarding dose setting information on the size of the next dose(s) to be delivered. For example, the user may enter carbohydrates to be eaten and current blood sugar (which alternatively may be obtained directly from sensor device 60 (FIG. 1A)), and health management application 40 may already know insulin on board. Using these parameters, a suggested medicine dose (e.g., a recommended insulin dose), calculated by the dose determination module, may be determined.

Figure 2:
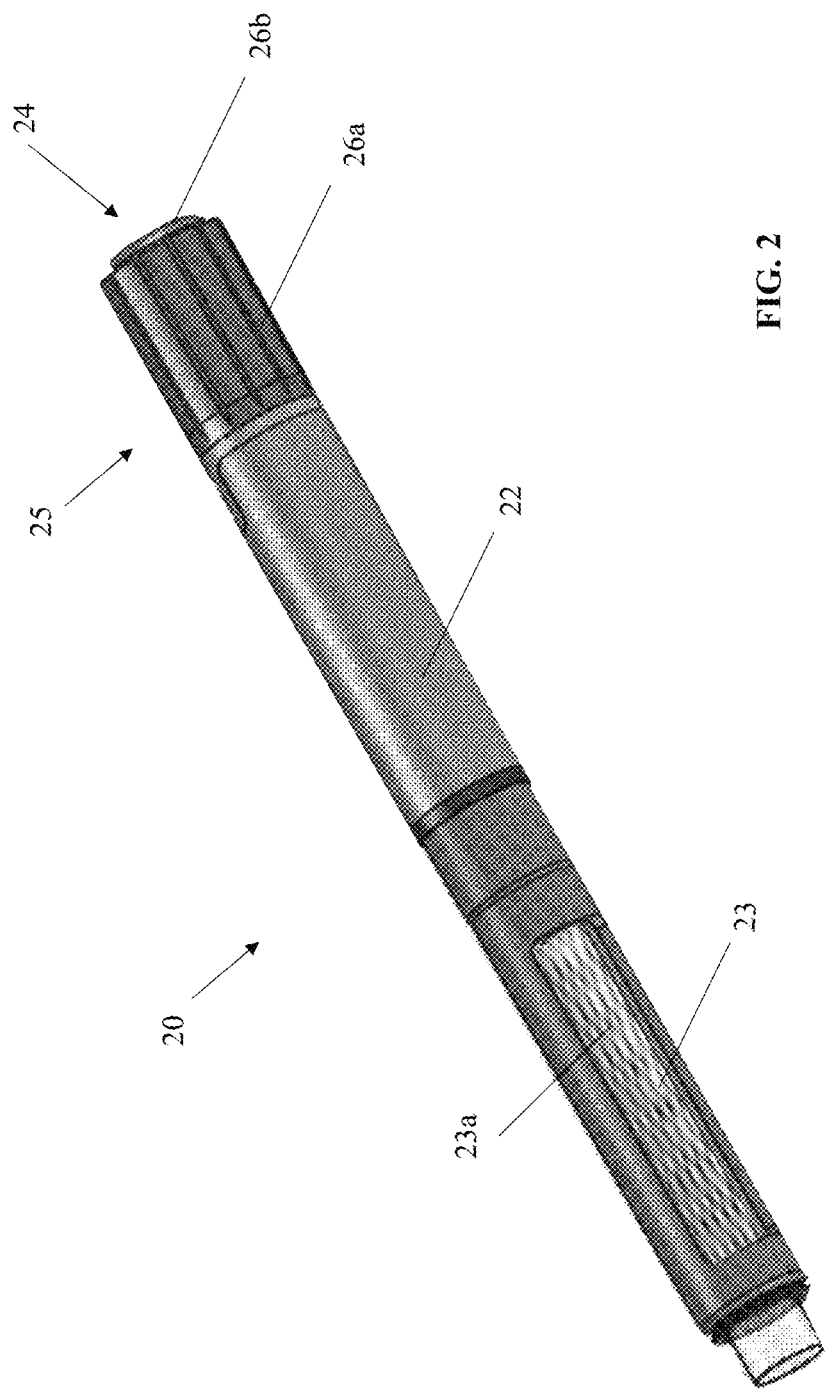
FIG. 2 is a perspective view of the medicine delivery device of FIG. 1A.

Referring to FIGS. 2, 3A, and 3B, pen 20 includes a body 22 configured to contain a medicine cartridge 23, e.g., an insulin cartridge. Pen 20 further includes a dose dispensing mechanism 24 to dispense (e.g., deliver) medicine contained in medicine cartridge 23 out of pen 20 (e.g., through needle 29) and a dose setting mechanism 25 to enable the selection and/or setting of a dose of medicine to be dispensed.

In aspects, in order to operate pen 20, the user first sets e.g., dials, a dose using a dose knob 26a of dose setting mechanism 25. For example, the dose may be adjusted up or down to achieve a desired dose amount prior to administration of the dose by rotating dose knob 26a in an appropriate direction. A dose indicator window 26d through body 22 is provided to enable a user to view the units set via dose knob 26a. Once the appropriate dose has been set, the user applies a force against a dose dispensing button 26b of dose dispensing mechanism 24 to begin dispensing. More specifically, to begin dispensing, the user presses against the portion of dose dispensing button 26b that protrudes from body 22 of pen 20 to thereby drive a driving element 26c, e.g., a drive screw 26c, of dose dispensing mechanism 24 against an abutment, e.g., piston 23b, of medicine cartridge 23 to dispense an amount of medicine from cartridge 23 through needle 29 into the user in accordance with the dose amount set by dose setting mechanism 25, e.g., dose knob 26a, during setting. Needle 29 may be integrated with pen 20 and/or cartridge 23 or may be removable and replaceable from pen 20 and/or cartridge 23.

Dose dispensing mechanism 24 of pen 20 can include a manually powered mechanism (user powered and/or mechanically biased), a motorized mechanism, or an assisted mechanism (e.g., a mechanism that operates partly on manual power and partly on motorized power). Regardless of the particular configuration of the dose dispensing mechanism 24, as noted above, when a force (e.g., a manual force, electrically-powered motor force, or combinations thereof) is applied to drive screw 26c of dose dispensing mechanism 24, drive screw 26c turn provides a force to urge medicine from medicine cartridge 23 to deliver the set or dialed dose. In aspects, dose dispensing mechanism 24 can be operated such that rotation and/or translation of the driving element, e.g., drive screw 26c, is facilitated by a variable tension spring or a variable speed motor to inject the dose over a specific time frame (e.g., 1 s, 5 s, etc.) to help reduce the pain of dosing and/or for other purposes.

Medicine cartridge 23 includes a vial body 23a defining an interior volume configured to retain a volume of medicine, e.g., insulin, therein, and a piston 23b sealingly and slidingly disposed within vial body 23a such that displacement of piston 23b within vial body 23a towards the dispensing end of vial body 23a forces medicine from the interior volume through dispensing opening 23c of cartridge 23 and needle 29 for injection into the user.

The rotation of the dose knob 26a during actuation drives (direct or indirect) rotation of drive screw 26c which rides within a nut (not explicitly shown) which is fixed to body 22 of pen 20. In this manner, rotation of drive screw 26c also results in translation of drive screw 26c (due to the pitched threading of drive screw 26c) towards medicine cartridge 23 to thereby drive piston 23b through vial body 23a to expel medicine from medicine cartridge 23 for injection into the user. The extent to which dose knob 26a extends from body 22 of pen 20 prior to actuation (which corresponds to the selected dose to be injected) defines the maximum amount of rotation of dose knob 26a and, thus, drive screw 26c during actuation; as such, the amount of medicine expelled from medicine cartridge 23 during actuation cannot exceed the selected dose amount.

Figure 5:
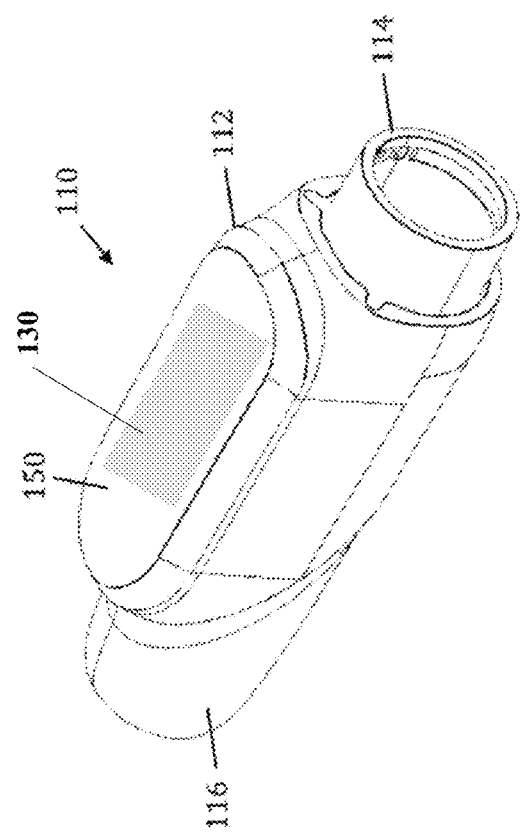
FIG. 5 is an enlarged, perspective view of the accessory device of FIG. 4.
Figure 4:
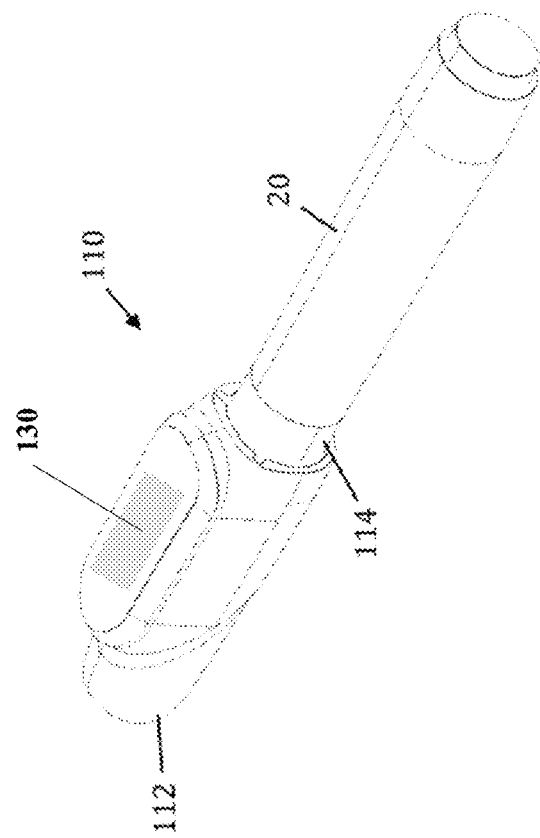
FIG. 4 is a perspective view of the medicine delivery device of FIG. 2 including an accessory device in accordance with the present disclosure coupled thereto.
Figure 6:
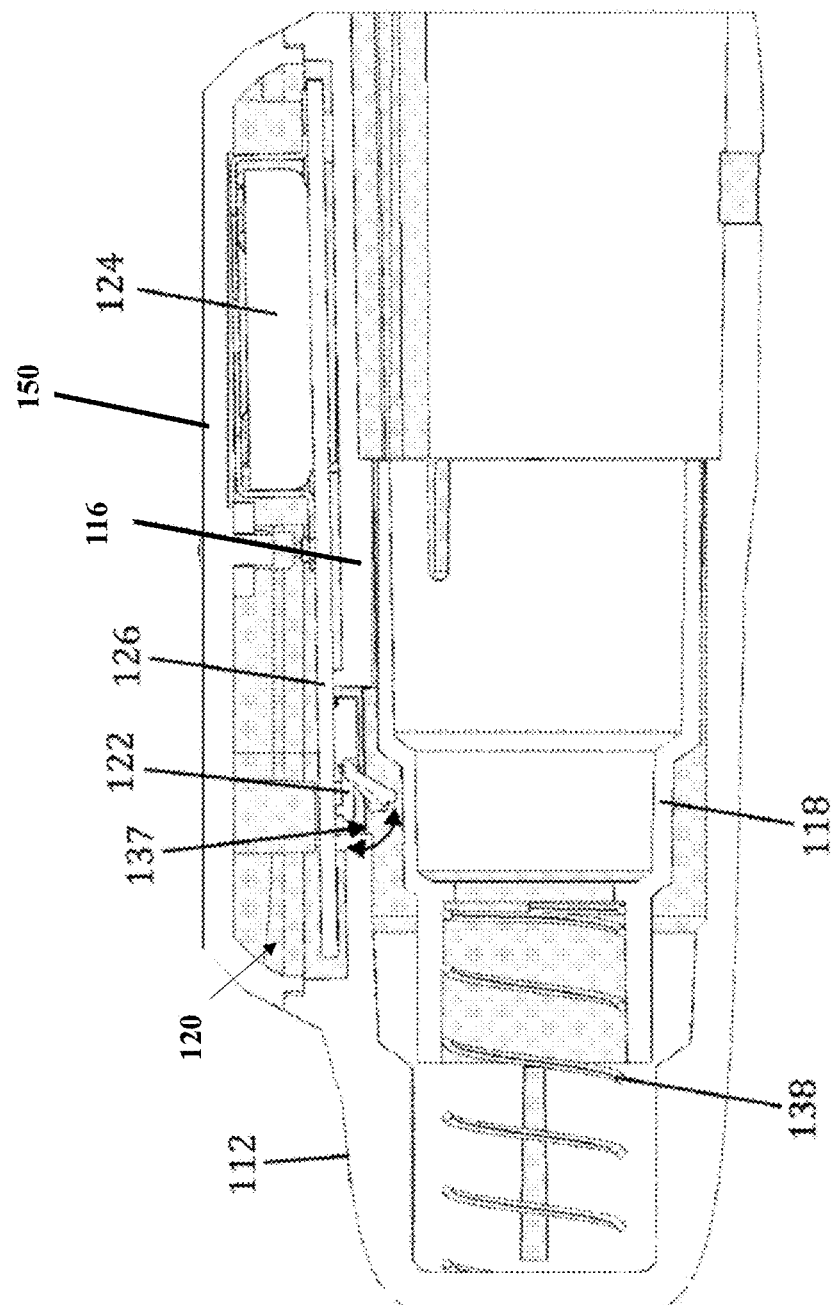
FIGS. 6-9 are longitudinal, cross-sectional views of the accessory device of FIG. 4 including various different detectors in accordance with the present disclosure.

Turning to FIGS. 4-6, as noted above, accessory device 100 may be configured as a cap 110 configured to selectively mechanically engage pen 20 to cover a dispensing end thereof, with or without needle 29 (FIGS. 3A and 3B) attached to pen 20. Cap 110 includes a body 112 defining a housing 116, a spring-loaded (e.g., via spring 138) slider 118 slidably disposed within housing 116, and a coupler adapter 114 (e.g., an appropriate coupler adapter 114 selected from a set of coupler adapters 114) releasably engageable with slider 118 and configured to enable use of cap 110 with various differently sized, shaped, and/or otherwise configured pens 20. Adapter 114 is configured to receive and engage pen 20 when the dispensing end of pen 20 is inserted into housing 116 to thereby retain cap 110 in engagement about pen 20 enclosing the dispensing end of pen 20 within housing 116.

Cap 110 further includes an electronics unit 120 that includes a detector (e.g., detection switch 122), a battery 124, a printed circuit board assembly (PCBA) 126, and a user interface 130. PCBA 126 may include a processor, a real-time clock, a storage module, and/or a communications module for wireless data transfer (e.g., via Bluetooth, WiFi, cellular network, and/or other suitable wireless communication protocol) to and/or from smartphone 30 (FIGS. 1A and 1B), although it is also contemplated that some of these components may be separate from PCBA 126 or omitted entirely. Electronics unit 120 is disposed (and, in aspects, sealed) within a cavity defined within body 112 of cap 110.

A cover 150 of body 112 encloses (and, in aspects, seals) the cavity and, thus, electronics unit 120 therein. Where a seal is provided, it may be hermetic to inhibit damage to electronics 120 from exposure to fluids, debris, etc. The output device(s) producing user interface 130 may form part of cover 150 to enable output (e.g., visual, audible, or other sensory output) from user interface 130, and/or cover 150 may include openings or other features to enable output of the output devices(s) producing user interface 130 on cover 150. The output device(s) producing user interface 130 may include a display screen, one or more LED's or other visual indicators, a speaker or other audio output device, a haptic feedback device, and/or other suitable user interface features configured to communicate information to a user.

When pen 20 is inserted into cap 110, pen 20 urges slider 118 to translate against the bias of spring 138 and interact with a deflectable arm 137 associated with detection switch 122 that extends into the travel path of slider 118. More specifically, the deflectable arm 137 of detection switch 122 may be biased to extend into the travel path (in the absence of slider 118) and to deflect out of the travel path in response to contact by and urging from slider 118 as slider 118 is translated within housing 116, e.g., under urging from the insertion of pen 20 into cap 110. Sufficient deflection of deflectable arm 137 closes (or opens) detection switch 122 such that a signal is detected by electronics unit 120 indicating that pen 20 has been inserted into cap 110. On the other hand, when pen 20 is removed from cap 110, slider 118 translates, under the bias of spring 138 back to its initial position, spaced-apart from deflectable arm 137. As such, deflectable arm 137 is returned to its initial, biased position extending into the travel path. As deflectable arm 137 is returned to this initial, biased position, detection switch 122 is opened (or closed) such that a signal is detected by electronics unit 120 indicating that pen 20 has been removed from cap 110.

Additional aspects and features of cap 110, configured for use in whole or in part in accordance with the aspects and features of the present disclosure (in whole or in part) can be found in U.S. Patent Application Pub. No. 2020/0327973, filed on Apr. 13, 2020 and titled "Intelligent Accessories for Medicine Dispensing Device," the entire contents of which are hereby incorporated herein by reference.

Continuing with reference to FIGS. 4-6, the signals indicating that pen 20 has been inserted into and/or removed from cap 110 can be utilized, e.g., by the processor of electronics unit 120 and/or via health management application 40 (FIG. 1A), to determine whether a dispensing event has occurred and, in aspects, what type of dispensing event, e.g., a priming event or an injection event, has occurred. For example, a dispensing event may be determined: based on removal of cap 110, based on replacement of cap 110, or based on removal of cap 110 without replacement for a defined period of time. The type of dispensing event may be determined based on the length of time cap 110 is removed, other factors, and/or other input data.

Figure 7:
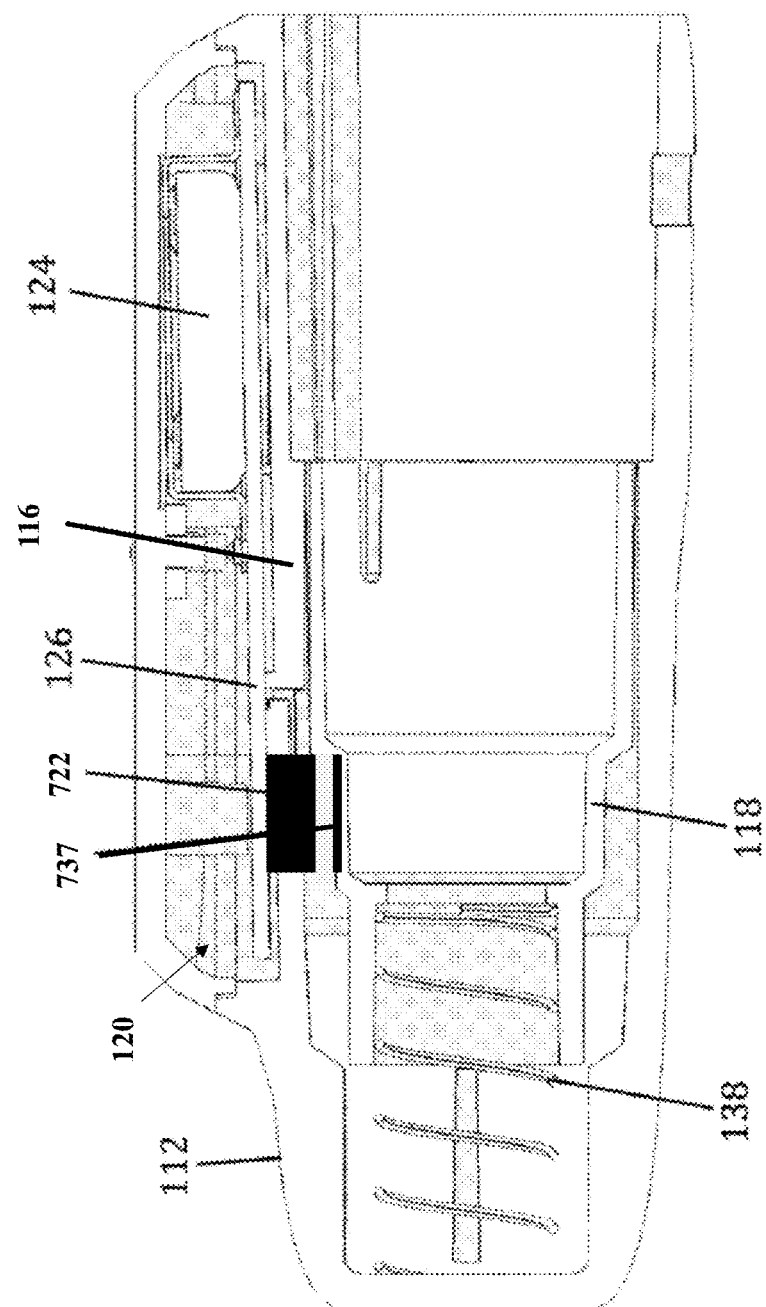

Referring to FIG. 7, in aspects, the detector may be a non-contact sensor 722 configured to detect movement of slider 118 (or a portion thereof, which may include a detectable element 737 to facilitate detection) into or out of approximation with sensor 722 to thereby enable detection of insertion or removal, respectively, of pen 20 (FIG. 4) to/from cap 110. For example, non-contact sensor 722 may be a hall effect sensor (wherein detectable element 737, if provided, is a magnetic element, or where slider 118 itself is a magnetic element), an optical sensor (wherein detectable element 737, if provided, is reflective, provides a detectable color, provides a detectable pattern, etc., or where slider 118 itself provides the same), a capacitive sensor (wherein detectable element 737, if provided, is electrically-conductive, or where slider 118 or other portion thereof is electrically-conductive), In aspects, non-contact sensor 722 is sealed, e.g., together with electronics unit 120 or separately therefrom.

Non-contact sensor 722, further still, may be an accelerometer or other suitable vibration sensor configured to sense vibrations associated with movement of slider 118 and/or movement of pen 20 (FIG.4) during insertion and engagement of pen 20 (FIG. 4) within cap 110 and/or disengagement and removal of pen (FIG. 4) from cap 110. Likewise, non-contact sensor 722 may be an audio sensor, e.g., a microphone, configured to sense sounds associated with movement of slider 118 and/or movement of pen 20 (FIG.4) during insertion and engagement of pen 20 (FIG. 4) within cap 110 and/or disengagement and removal of pen (FIG. 4) from cap 110.

Other suitable locations for sensor 722 are also contemplated depending upon a particular purpose such as, for example, to sense movement and/or other properties of spring 738 rather than slider 118. In aspects wherein spring 738 is a coil spring, for example, sensor 722 may be configured to sense movement, e.g., approximation or spacing, of the rungs of spring 738, e.g., optically, or may be configured to sense an amount of compression of spring 738, e.g., electrically based on a change in capacitance of spring 738 as it is compressed or extended. As movement of spring 738 is related to whether pen 20 (FIG. 4) is inserted or removed from cap 110, sensing movement of spring 738 can thus provide similar information as detailed above with respect to slider 118.

Figure 8:
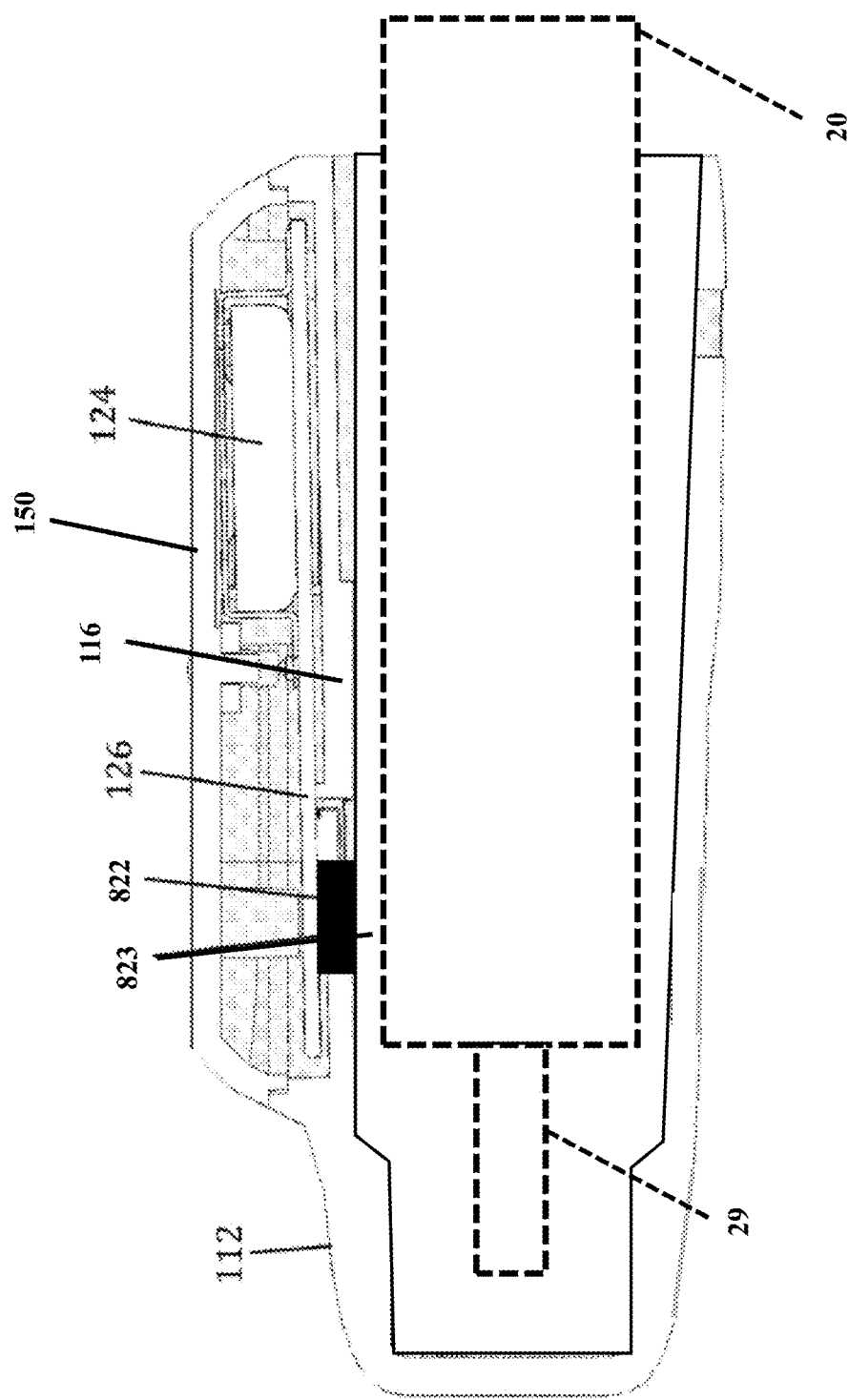
Figure 9:
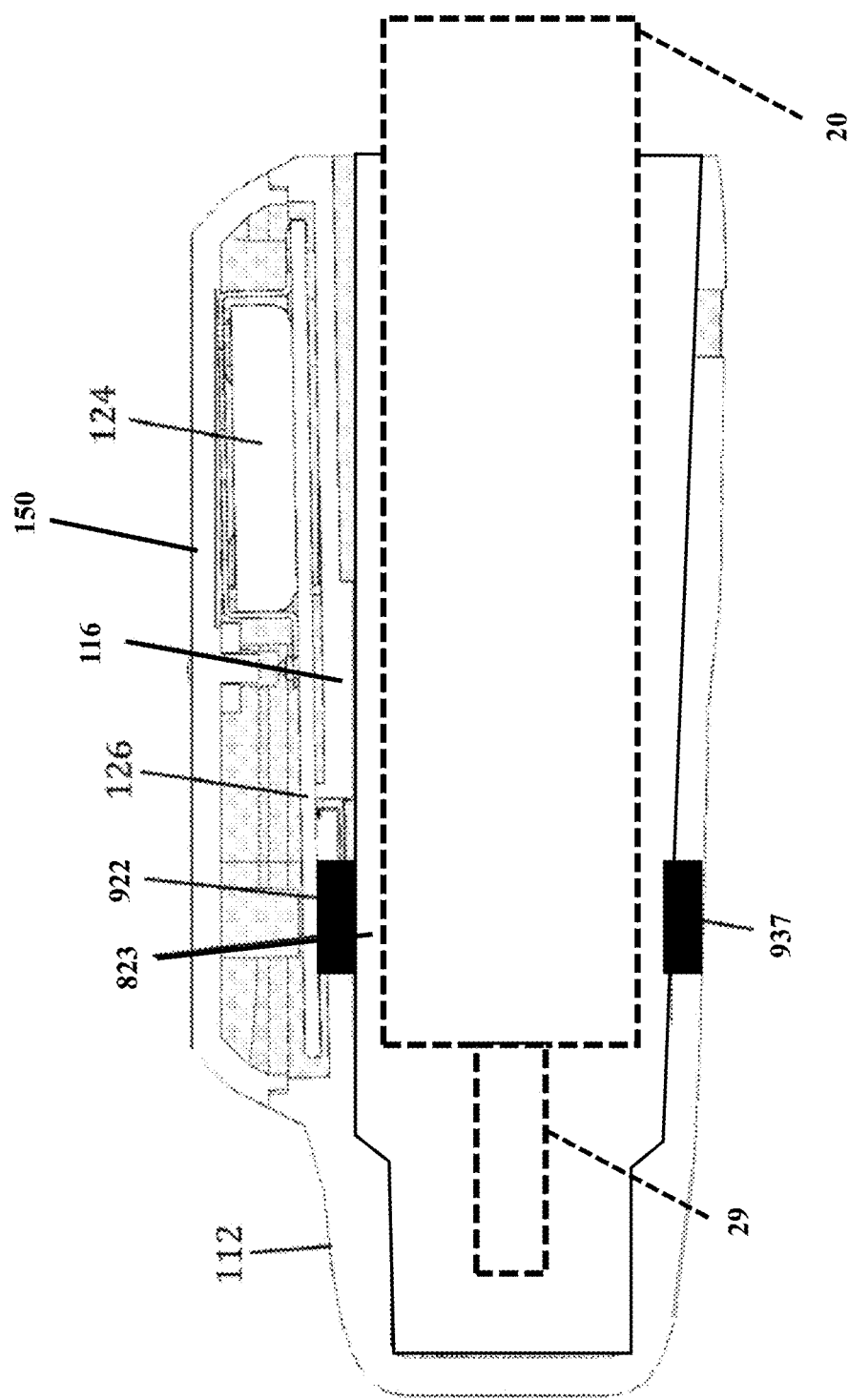

With reference to FIGS. 8 and 9, in aspects, rather than providing slider 118 (and/or spring 738) to enable detection of insertion and/or removal of pen 20, detector may include a sensor 822 or 922 configured to sense one or more properties of the interior cavity 823 defined by housing 116 of cap 110 to enable detection of the insertion and/or removal of pen 20. Referring in particular to FIG. 8, sensor 822 may be configured to sense the presence or absence of pen 20 (or a portion thereof) within interior cavity 823, and may accomplish this by being configured as an optical sensor, a vibration sensor, an audio sensor, a magnetic sensor (where a portion of pen 20 is magnetic), a capacitive sensor (where a portion of pen 20 is electrically-conductive), a moisture sensor (sensing medicine on needle 29 or a dispensing end of pen 20), etc. Referring in particular to FIG. 9, in aspects, sensor 922 may include a second component 937 that cooperates with sensor 922 to facilitate detection. Second component 937 may be disposed opposite sensor 922 across cavity 823 and may be, for example, a reflector (for an optical sensor), receiver (e.g., wherein sensor 922 is a transmitter), or other reference component to facilitate sensor 922 detecting whether pen 20 is disposed within cavity 823 or removed therefrom based on whether a signal is capable of being communicated between sensor 922 and second component 937.

Continuing with reference to FIGS. 8 and 9, in aspects, sensor 822 and/or sensor 922 may be configured, in addition or as an alternative to detecting the presence or absence of pen 20, to determine one or more features of pen 20 and/or the medicine or medicine cartridge 23 (FIGS. 3A and 3B). For example, sensor 822 and/or sensor 922 may be configured to detect a size, shape, feature, or other physical characteristic of the exterior of pen 20, which can be communicated to enable determination of a manufacturer and/or type of pen 20 (or cartridge 23 (FIGS. 3A and 3B) therein), e.g., via health management application 40 (FIG. 1A). As another example, sensor 822 and/or sensor 922 may be configured to detect an amount and/or property (clarity, for example), of medicine, e.g., insulin, in pen 20, to enable communication of the same to health management application 40 (FIG. 1A).

Figure 10:
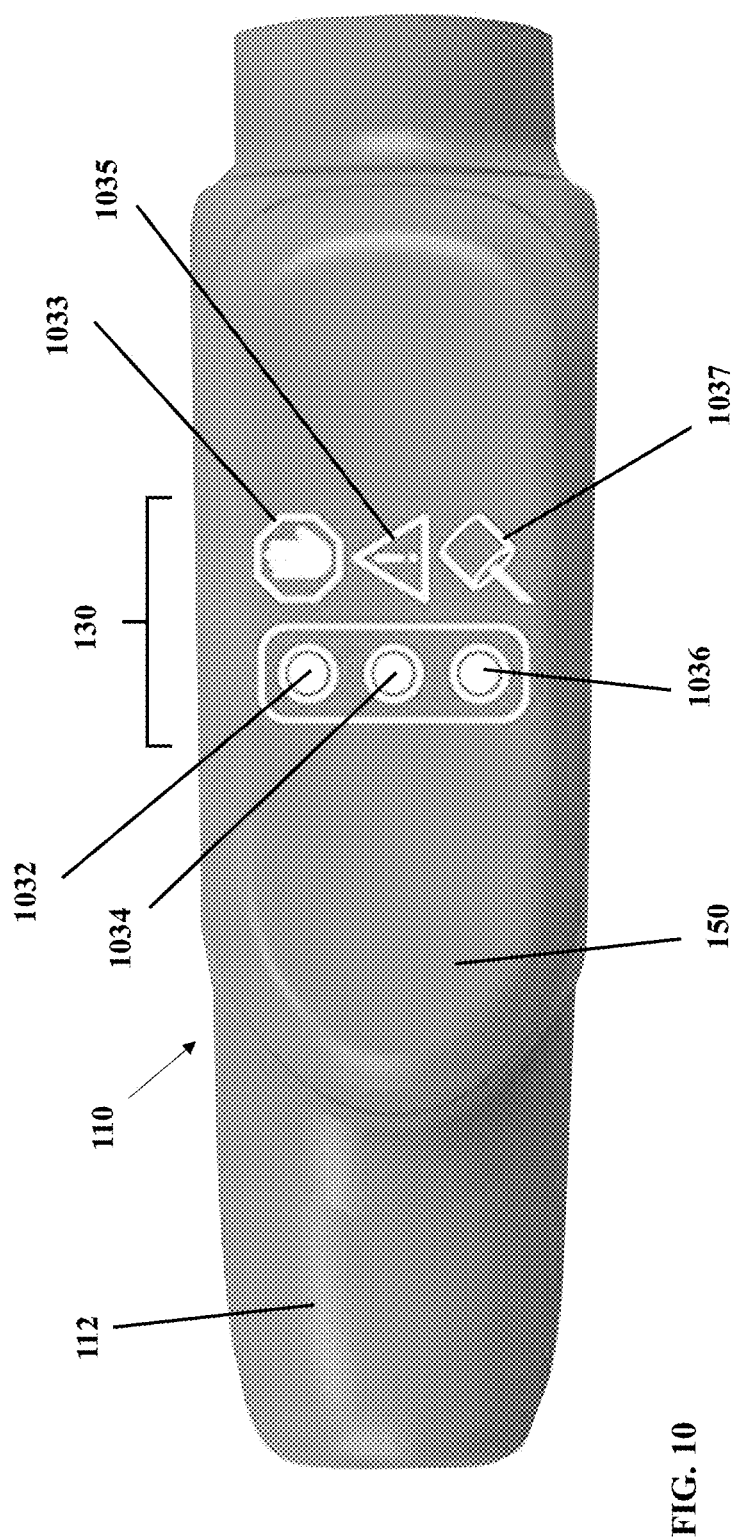
FIG. 10 is a top view of the accessory device of FIG. 4 including a user interface in accordance with the present disclosure.

Turning to FIG. 10, as noted above, cap 110 includes a user interface 130 to enable the output of information to a user. User interface 130 may be disposed on cover 150 of body 112 of cap 110 or may be otherwise disposed, e.g., at another location on body 112. In aspects, cap 110 is configured to independently determine and output and/or to communicate with health management application 40 (FIG. 1A) to enable output of relevant information to the user via user interface 130 of cap 110. For example, user interface 130 may provide an output to the user to inform the user whether it is safe to dose. In aspects, user interface 130 is a display screen that enables display and, in aspects, input (e.g., via touch-screen functionality), of information such as, for example, by displaying a version of health management application 40 (FIG. 1A). However, the power available for user interface 130 may be limited in an effort to conserve battery and, thus, in other aspects, user interface 130 may include two lights 1032, 1036, or three lights 1032, 1034, 1036, e.g., LED's, and associated symbology 1033, 1035, 1037, respectively, adjacent or otherwise associated with each light 1032, 1034, 1036, as detailed below.

In aspects, the lights 1032, 1034, 1036 may be red, yellow, and green lights, respectively, arranged in that order (or red and green where only lights 1032, 1036 are provided). Although the red/yellow/green and red/green light schemes are generally known and utilized for various purposes, it has been found that in certain situations, such as with respect to indicating whether it is safe to dose, the red/yellow/green and red/green light schemes may be confusing, even with certain symbology associated therewith. For example, where a green light is illuminated, the user may be confused as to whether the green light is an indication that the user is in compliance and, thus, does not need to dose, or whether the indication is telling the user that it is safe to dose. Likewise, where a red light is illuminated, the user may likewise be confused as to whether the red light is indicating that the user is not in compliance and needs to dose, or whether the indication is telling the user that it is not safe to dose.

To obviate the above confusion, lights 1032, 1034, 1036 (or at least lights 1032, 1036 (whether only lights 1032, 1036 are provided or all three lights 1032, 1034, 1036 are provided)) and associated symbology 1033, 1035, 1037, respectively, are provided in a manner that clarifies the action to be taken. For example, symbol 1037 is positioned adjacent green light 1036 (or otherwise associated therewith such as, for example, where symbol 1037 is overlayed or otherwise positioned relative to green light 1036 such that symbol 1037 is illuminated when green light 1037 is illuminated). Symbol 1037 indicates the action to be taken; that is, the action that it is safe to proceed when the green light 1036 is illuminated. Symbol 1037 may be an image or other representation of a needle (as shown), a syringe, an injection pen, an amount of medicine, or other suitable symbol indictive of the delivery of medicine to the user. Symbol 1033 is positioned adjacent (or otherwise associated with) red light 1032 and indicates the action to be taken; that is, "stop" or "do not proceed" when the red light 1032 is illuminated. Symbol 1033 may be an image or other representation to "stop" such as, for example, a stop hand signal (as shown), a stop sign, or other suitable symbol indicating to the user to stop or take no action because it is not safe to dose. In configurations where yellow light 1034 is provided, symbol 1035 is positioned adjacent (or otherwise associated with) yellow light 1034 and provides an indication of caution, e.g., via a caution sign or other suitable symbol, thus indicating the user to proceed with caution because it is not recommended to dose but may acceptable.

Control of, e.g., selective illumination of, lights 1032, 1034, 1036 may be provided by electronics unit 120 (FIG. 6) based on determinations made by electronics unit 120 (FIG. 6) and/or from a connected device, e.g., smartphone 30 running health management application 40 (FIG. 1A)). For example, health management application 40 (FIG. 1A) may communicate to electronics unit 120 (FIG. 6) of cap 110 a log of one or more prior injections, an interval between doses, and/or a schedule of doses, etc. to enable electronics unit 120 (FIG. 6) to illuminate the appropriate light 1032, 1034, 1036 based on the information received. Alternatively or additionally, electronics unit 120 (FIG. 6) may determine when a dose occurs (as detailed above, for example, or in any other suitable manner), determine an interval between doses, and, based thereon, illuminate the appropriate light 1032, 1034, 1036. In aspects, the medicine, e.g., insulin, manufacturer sets the interval and/or schedule for the particular medicine utilized. Health management application 40 (FIG. 1A) and/or electronics unit 120 (FIG. 6) may additionally or alternatively utilize CGM data, other physiological data, and/or other input data (e.g., meal data, exercise data, etc.), to determine whether it is safe to dose. A control implementation of lights 1032, 1034, 1036 in accordance with the present disclosure is detailed below with reference to FIG. 11, although other suitable control implementations are also contemplated.

Figure 11:
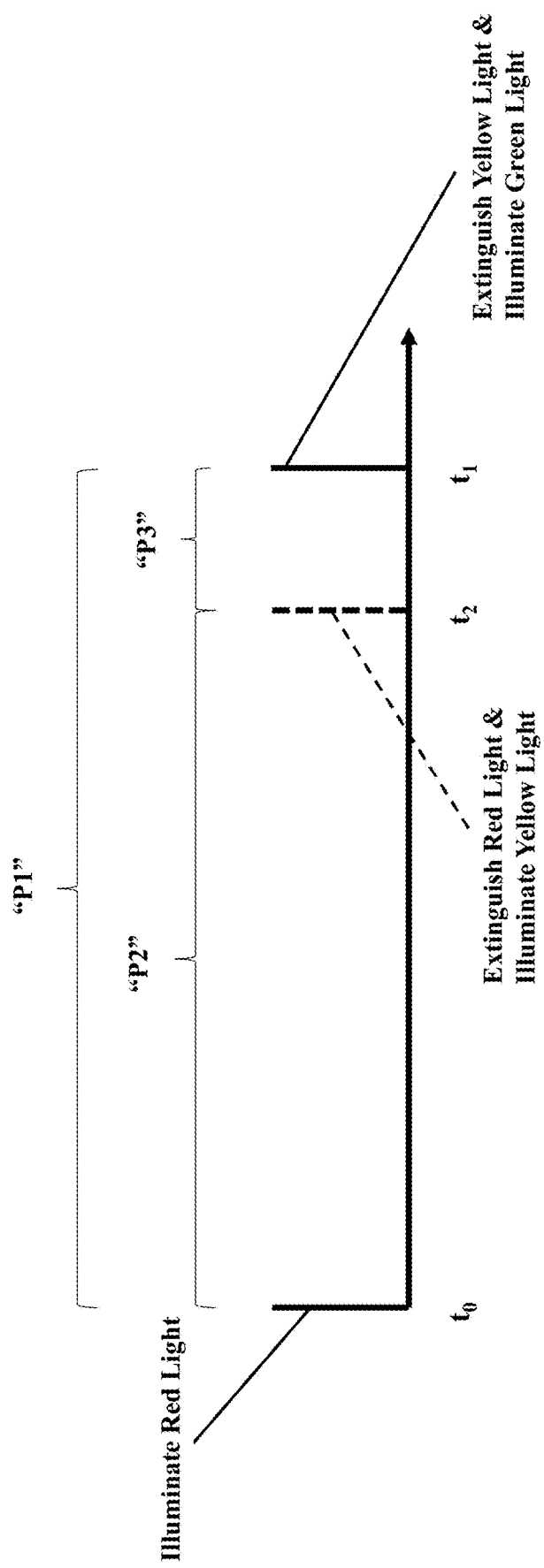
FIG. 11 is graphical representation of a timeline for dose recommendation indicators in accordance with the present disclosure.

With additional reference to FIG. 11, following each dose, e.g., a dose at time "$t_0$," a time after which it is safe to dose is set as "$t_1$," thus defining a time period "P1," wherein $P1=t_1-t_0$. Period of time "P1" may be a pre-determined period of time or a dynamically determined period of time determined, for example, based on CGM data, other physiological data, and/or other input data or other physiological data. As green light 1036 and corresponding symbol 1037 indicate to the user that it is safe to dose, green light 1036 is illuminated at time "$t_1$," only after time period "P1" has elapsed, and only until a subsequent dose is logged. With green light 1036 illuminated, a dose is logged when cap 110 is removed from pen 20 (FIG. 4), assuming any other criteria, e.g., the length of time cap 110 is removed, the other factors, etc. as detailed above, are met.

In addition to the "safe to dose" time "$t_1$," there is a time "$t_2$" before which it is not safe to dose, thus defining a second period of time "P2," wherein $P2=t_2-t_0$. As red light 1032 and corresponding symbol 1033 indicate to the user that it is not safe to dose, red light 1032 is illuminated at time "$t_0$" and remains illuminated throughout period "P2" until time "$t_2$." Period of time "P2" may be pre-determined or dynamically determined. In aspects, if cap 110 is removed from pen 20 (FIG. 4) while red light 1032 is illuminated, an assumption is made that a dose was not taken regardless of the length of time cap 110 is removed, the other factors, etc. and, thus, no dose is logged. This assumption may be overridden based on other factors, input information, sensed data, etc.

In aspects where no yellow light 1034 is provided, $t_1=t_2$ and P1=P2. However, it has been found that there may be a time period "P3" defined between times "$t_2$" and "$t_1$" wherein, while it is not recommended to dose, it may be acceptable to dose in certain circumstances, for example, where the user is not able to dose for an extended length of time after expiration of time period "P1," e.g., due to a social commitment, work commitment, personal reason, or any other reason. Time period "P3" may be pre-determined or dynamically determined, and is defined in relation to "P1" and "P2" according to the equation P1=P2+P3.

In aspects where time period "P3" is utilized, red light 1032 is extinguished at time "$t_2$" and yellow light 1034 is illuminated. Yellow light 1034, indicating that the user should proceed with caution because it is not recommended to dose but may be acceptable, remains illuminated for the duration of time period "P3" until time "$t_1$," after which yellow light 1034 is extinguished and green light 1036 is illuminated until the next dose is logged. With yellow light 1034 illuminated, a dose is logged when cap 110 is removed from pen 20 (FIG. 4), assuming any other criteria, e.g., the length of time cap 110 is removed, the other factors, etc. as detailed above, are met. In aspects, the criteria for logging a dose upon removal of cap 20 with yellow light 1034 illuminated may differ from the criteria for logging a dose upon removal of cap 20 with green light 1036 illuminated.

Although the above control implementation of lights 1032, 1034, 1036 describes the illumination and extinguishing of lights 1032, 1034, 1036 in an activated condition, it is noted that the control implementation may not be activated at all times but, rather, may have a dormant condition. That is, in the dormant condition, all lights may be extinguished, e.g., to conserve battery and inhibit distraction. For example, the above control implementation may be activated from the dormant condition when motion is sensed, indicating that pen 20 (FIG. 4) with cap 110 thereon is being manipulated, e.g., picked up, removed from the user's pocket, etc. As another example, the above control implementation may additionally or alternatively be activated from the dormant condition when cap 110 is removed from pen 20 (FIG. 4). In other aspects, in addition or as an alternative to the above, the control implementation may switch between the activated and dormant conditions based upon the time of the day, the user's schedule or location (e.g., obtained from connected devices), based on physiological feedback data (e.g., obtained from connected devices), etc. In other aspects, the control implementation may be set to or may always remain in the activated condition.

In aspects, rather than providing user interface 130 on cap 110, user interface 130 may be provided on body 22 of pen 20 (see FIGS. 3A and 3B) to convey information to the user similarly as detailed above. In such aspects, or any other aspects detailed herein, pen 20 (see FIGS. 3A and 3B) may be configured to sense an amount of dose selected and/or dispensed, and/or to communicate with a connected device, e.g., cap 110, smartphone 30 running health management application 40 (FIG. 1A)), etc., such as, for example, detailed in U.S. Pat. No. 9,672,328, issued on Jun. 6, 2017 and titled "Medicine Administering System Including Injection Pen and Companion Device," the entire contents of which are hereby incorporated herein by reference.

The various aspects and features disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described functional and/or operational aspects may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" or "processing unit" as used herein may refer to any of the foregoing structure or any other physical structure suitable for implementation of the described techniques. Also, the techniques could be fully implemented in one or more circuits or logic elements.

While several aspects of the present disclosure have been detailed above and are shown in the drawings, it is not intended that the disclosure be limited thereto, as it is intended that the disclosure be as broad in scope as the art will allow and that the specification be read likewise. Therefore, the above description and accompanying drawings should not be construed as limiting, but merely as exemplifications of particular aspects. Those skilled in the art will envision other modifications within the scope and spirit of the claims appended hereto.

What is claimed is:

1. An accessory for use with a medicine delivery device, the accessory comprising:
 a body configured to attach to the medicine delivery device; and
 a user interface disposed on the body and configured to communicate information to a user, the user interface including:
  a first light configured to be selectively illuminated;
  a first symbol associated with the first light, the first symbol depicting a medicine delivery device performing a medicine delivery action, wherein the first light and the first symbol together indicate that it is safe to perform the medicine delivery action using the medicine delivery device when the first light is illuminated; and
  a second light configured to be selectively illuminated.

2. The accessory according to claim 1, wherein the first light is a green light and the second light is a red light.

3. The accessory according to claim 1, wherein the user interface further includes a second symbol associated with the second light, the second light and the second symbol together providing an indication.

4. The accessory according to claim 3, wherein the second light is a red light and the second symbol is a stop symbol such that, when the red light is illuminated, the indication is to stop and not proceed with using the medicine delivery device.

5. The accessory according to claim 1, wherein the body is configured to releasably attached to the medicine delivery device.

6. The accessory according to claim 5, wherein the body is a cap configured to releasably cover a dispensing end of the medicine delivery device.

7. The accessory according to claim 6, further comprising at least one detector disposed within the body and configured to detect at least one of attachment of the cap with the medicine delivery device or detachment of the cap from the medicine delivery device.

8. The accessory according to claim 1, wherein the user interface further includes a third light configured to be selectively illuminated.

9. The accessory according to claim 8, wherein the first light is a green light, the second light is a red light indicating it is not safe to use the medicine delivery device to dose, and the third light is a yellow light indicating proceed with caution.

10. An accessory for use with a medicine delivery device, the accessory comprising:
 a body configured to attach to the medicine delivery device;
 an electronics unit disposed within the body, the electronics unit configured to at least one of receive or determine, with respect to a prior dose at time t0, each of: a first time t1 after which it is safe to dose, a second time t2 before which it is not safe to dose, and a time period P that is defined from second time t2 to first time t1 and represents when it is not recommended to dose but when dosing is acceptable; and
 a user interface disposed on the body in communication with the electronics unit, the user interface including a green light, a red light, and a yellow light, the electronics unit configured to control the user interface to:
  illuminate the red light between time t0 and time t2;
  extinguish the red light and illuminate the yellow light at time t2;
  maintain the yellow light for time period P from time t2 to time t1; and
  extinguish the yellow light and illuminate the green light at time t1.

11. The accessory according to claim 10, wherein the electronics unit is further configured to control the user interface to maintain the green light from time t1 until a subsequent dose is logged.

12. The accessory according to claim 10, wherein the times t0, t1, and t2 are relative times or clock times.

13. The accessory according to claim 10, wherein the body is a cap configured to releasably cover a dispensing end of the medicine delivery device.

14. The accessory according to claim 13, further comprising at least one detector disposed within the body and configured to detect at least one of attachment of the cap with the medicine delivery device or detachment of the cap from the medicine delivery device.

15. The accessory according to claim 14, wherein the electronics unit is configured to determine or receive a determination that a dose from the medicine delivery device has occurred based at least upon at least one of an attachment of the cap or a detachment of the cap.

16. The accessory according to claim 15, wherein the determination that a dose from the medicine delivery device has occurred is further based upon which light is illuminated.

17. The accessory according to claim 16, wherein no determination that a dose from the medicine delivery device has occurred is made despite the at least one of attachment of the cap or detachment of the cap when the red light is illuminated.

18. The accessory according to claim 15, wherein the determination that a dose from the medicine delivery device has occurred is made based upon the at least one of attachment of the cap or detachment of the cap and other criteria when either the green light or the yellow light is illuminated.

19. The accessory according to claim 18, wherein the criteria when the green light is illuminated are different from the criteria when the yellow light is illuminated.

* * * * *